United States Patent [19]

Yoshida et al.

[11] 3,985,722

[45] Oct. 12, 1976

[54] PROCESS FOR PREPARING N-HIGHER ALIPHATIC ACYL DERIVATIVES OF AMINO ACIDS, PEPTIDES OR PROTEINS

[75] Inventors: Ryonosuke Yoshida, Kamakura; Takashi Shishido, Kawasaki, both of Japan

[73] Assignee: Ajinomoto Co., Inc., Tokyo, Japan

[22] Filed: Dec. 9, 1974

[21] Appl. No.: 530,989

[30] Foreign Application Priority Data

Dec. 12, 1973 Japan.............................. 48-138975
June 8, 1974 Japan.............................. 49-64589

[52] U.S. Cl........................ 260/112 R; 260/112 G; 260/112.5 R; 260/309.6; 260/313.1; 260/326.14 T; 260/404; 260/518 R; 260/404.5; 260/519; 260/534 R; 260/534 C; 260/534 E; 260/534 G; 260/534 L; 260/534 S; 260/535 R

[51] Int. Cl.².................... C07C 103/52; C07G 7/00

[58] Field of Search................. 260/112.5 R, 112 R, 260/112 G, 309.6, 313 T, 326.14 T, 518 R, 519, 534 R, 534 C, 534 E, 534 G, 534 L, 534 S, 535 R, 404, 404.5

[56] References Cited

UNITED STATES PATENTS 3,124,564   3/1964   McKay............................ 260/112.5

OTHER PUBLICATIONS

Kenner, Chem. Soc. Spec. Publ. (London), 2, 107–111 (1955).
E. Schroder and K. Lubke, "The Peptides", vol. 1, Academic Press, New York, 1965, p. 93.

*Primary Examiner*—Lewis Gotts
*Assistant Examiner*—Reginald J. Suyat
*Attorney, Agent, or Firm*—Oblon, Fisher, Spivak, McClelland & Maier

[57] ABSTRACT

A mixed acid anhydride consisting of higher fatty acid having 6 to 22 carbon atoms and sulfuric anhydride is reacted with amino acids, peptides or proteins in the presence of a base to form N-higher aliphatic acyl derivatives of amino acids, peptides or proteins respectively in good yield. The reaction mixture comprises N-acylated-amino acids, peptides or -proteins and sulfate salts and may be directly used as detergent.

10 Claims, No Drawings

PROCESS FOR PREPARING N-HIGHER ALIPHATIC ACYL DERIVATIVES OF AMINO ACIDS, PEPTIDES OR PROTEINS

BACKGROUND OF THE INVENTION

Field of the Invention

This invention relates to a novel process for preparing N-acyl derivatives of free amino group containing organic compounds in which the acyl groups are radicals of fatty acids having 6 to 22 carbon atoms, and particularly to a process for preparing N-acylated-amino acids, -peptides and -proteins without accompanying formation of by-products which are undesirable in the detergent field.

DESCRIPTION OF PRIOR ART

The salts of N-higher aliphatic acyl derivatives of amino acids, peptides and proteins are effective surfactants and may be widely utilized as detergents, dispersing and emulsifying agents. Especially, salts of N-lauroyl sarcosine, salts of N-higher aliphatic acyl-$\beta$-alanine, salts of N-higher aliphatic acyl-glutamic acid and salts of coconut oil fatty acyl peptide are useful as detergents and as bases or additives for cosmetics, because of their desirable properties such as mildness on the human skin, good foaming property and favorable emulsification characteristics.

N-Higher aliphatic acyl derivatives of amino acids, peptides or proteins have been commercially prepared by acylating amino acids, peptides or proteins (hereinafter, amino acids, peptides or proteins are referred to as amino acid related compounds) with a higher fatty acid chloride in aqueous alkaline media. The chief disadvantage of this method is to obtain a reaction mixture containing a chloride salt such as sodium chloride, with the salt of the desired N-acylated amino acid related compound in which the presence of a chloride salt is undesirable as surfactant, especially as a detergent.

The salts of N-acyl amino acid related compounds are most effectively used as detergents when substantially free of the chloride salt formed as by-product in the fatty acid chloride method. For purposes of utilizing a compound related to sodium salt of N-acyl amino acid as a detergent, it is necessary that the reaction mixture first be acidified to precipitate the N-acylated amino acid related compounds which are then separated and purified, and neutralized with sodium hydroxide to convert to the corresponding sodium salts. Accordingly, the reaction mixture obtained by the acyl chloride method cannot be used as a detergent, and so the separation and purification steps and subsequent neutralization step of the desired product can not be avoided for this purpose.

It has heretofore been known to employ a sodium acetyl sulfate as an acetylating agent, which may be obtained by reacting sulfuric acid with a mixture of sodium acetate and acetic anhydride. Whereas, when sulfuric anhydride is reacted with acetic acid or butyric acid, the resulting mixed acid anhydride is unstable and tends to convert into $\alpha$-sulfoacetic acid or $\alpha$-sulfobutyric acid. Also, when sulfuric anhydride is reacted with a higher fatty acid such as lauric or palmitic acid, similarly the corresponding $\alpha$-sulfofatty acid is formed. For this reason, no attempt has been made to employ a mixed acid anhydride consisting of higher fatty acid and sulfuric anhydride as an acylating agent of amino acid related compounds.

SUMMARY OF THE INVENTION

It is an object of this invention to provide a simple and convenient process for preparing N-higher aliphatic acyl derivatives of amino acid related compounds by employing a higher fatty acid-sulfuric acid mixed acid anhydride (hereinafter, referred to as F.S.M.A) as an acylating agent, which process does not result in the formation of a chloride salt as in the acyl chloride method.

It has now been found that when 1 mole of a higher fatty acid is reacted with 1 to 2 moles of sulfuric anhydride in an organic solvent at low temperatures below 40°C, F.S.M.A is prepared in a stable state. The reaction between an amino acid, peptide or protein and the F.S.M.A prepared thus, in the presence of a base gives a good yield of the desired product.

DETAILED DESCRIPTION OF THE INVENTION

According to this invention, the N-acyl derivatives of an amino acid protein or peptide may be prepared in good yield by suspending or dissolving an amino acid protein or peptide in an aqueous or non-aqueous solvent, and by adding F.S.M.A simultaneously with a calculated amount of base drop by drop.

For example, when F.S.M.A is added to an aqueous sodium hydroxide solution of the amino acid, protein or peptide, the resultant reaction solution will comprise the corresponding sodium salt of N-acylated amino acid protein, or peptide and sodium sulfate, which may per se be directly employed as a liquid detergent composition after an appropriate adjustment of the pH with sulfuric acid. Alternatively, it may be prepared directly in the form of a powdered detergent simply by application of conventional spray-drying methods.

The F.S.M.A which may be employed as an acylating agent in the present process may be obtained by reacting a fatty acid having 6 to 22 carbon atoms, or a salt thereof, with sulfuric anhydride or a sulfuric anhydride complex, in the presence or absence of a non-aqueous solvent. Suitable acylating agents may be prepared by suspending or the dissolving fatty acid or salt thereof in a non-aqueous solvent and by addition of 1 to 2 moles, preferably 1 to 1.5 moles of sulfuric anhydride or complex thereof, drop by drop at temperatures ranging from −20°C to 40°C. Preferred temperatures for the reaction between the free fatty acid and the sulfuric anhydride are in the range of −5° to 5°C while those for the reaction between the fatty acid salt and the sulfuric anhydride are in the range of 0° to 30°C. After completion of the reaction, it is desirable to neutralize the reaction mixture with an alkali or amine such as trimethylamine, triethylamine or tributylamine, or otherwise to maintain the reaction mixture at a low temperature below 20°C, to prevent the formation of undesirable $\alpha$-sulfofatty acid. The most favourable methods for synthesizing F.S.M.A are as follows; reacting tertiary amine salt of a fatty acid with sulfuric anhydride, or by neutralization of the reaction product of a fatty acid and sulfuric anhydride with tertiary amine.

Suitable higher fatty acids which may be employed in the preparation of F.S.M.A in the present process, include the natural and synthetic fatty acids having 6 to 22 carbon atoms. Suitable examples of such fatty acids the are saturated or unsaturated fatty acids, such as caprylic acid, capric acid, lauric acid, myristic acid, palmitic acid, stearic acid, oleic acid, linoleic acid, or mixtures of fatty acids which are derived from natural fats and, such as coconut oil, corn oil, olive oil, palm oil, tallow oil, hydrogenated tallow oil, soybean oil and cottonseed oil. The corresponding salts of the fatty acids, are suitable, such as the sodium, potassium, calcium or magnesium salts or organic amine salts, such as trimethylamine, triethylamine and pyridine salts. Especially, suitable are the organic amine salts which are soluble in a non-aqueous solvent, are preferably employed.

Suitable examples of non-aqueous solvents are the halogenated hydrocarbons, such as 1.2-dichloroethane, chloroform, trichloroethane and tetrachloride; ethers, such as dioxane and tetrahydrofuran; hydrocarbons, such as petroleum ether, hexane, benzene and toluene; dimethylformamide, dimethylsulfoxide or the like.

In addition to sulfuric anhydride (sulfur trioxide), sulfuric acid complexes such as dioxane-sulfur trioxide, dimethylformamide-sulfur trioxide, dimethylaniline-sulfur trioxide and pyridine-trioxide may also be employed.

Examples of the amino acid related compounds which may be acylated with F.S.M.A in the present process are $\alpha$, $\beta$ or $\omega$-amino acids, salts thereof, ester thereof; peptide, ester thereof, amide thereof; polyamino acid and protein. The peptide protein used should contain a free amino group.

Examples of suitable amino acids include taurine, glycine, $\alpha$-alanine, $\beta$-alanine, sarcosine, valine, leucine, isoleucine, methionine, cystine, cysteine, phenylalanine, tyrosine, tryptophan, threonine, serine, proline, $\omega$-aminocaproic acid, glutamic acid, aspartic acid, oxyglutamic acid, methylglutamic acid, cysteic acid, homocysteic acid, lysine, ornithine, histidine, arginine, mixtures thereof, $C_1 - C_{22}$ alkyl ester of these amino acids. Examples of suitable proteins include casein, gelatin, yeast, soybean protein, proteins separated from the squeezed serum of vegetable seed oil, proteins contained in fish processed drainage and the extracted protein of microorganisms which are generally used in amino acid fermentation. Also, examples of suitable peptides include synthetic peptides such as glycyl-DL-alanine, L-lysyl-L-valine, L-lysyl-L-valine ethyl ester, glycyl-glycyl-glycine and polylysine; and peptides having 2 to 12 average peptide length which may be prepared from vegetable proteins, animal proteins such as fish protein, microorganisms for use in fermentation or yeast by partial hydrolysis with an acid, alkali or proteolytic enzyme by the well-known process in itself. For example, peptides having an average peptide length of 2–12 may be conveniently prepared by the following method: The proteins separated from the squeezed serum of vegetable seed oil are heated at 100° – 120°C for 10 – 24 hours in the presence of below 7 times by weight hydrochloric acid. As another instance, the dried microorganisms of amino acid fermentation which contains 50 – 60% proteins are immersed in water or in a dilute alkaline solution (such as sodium hydroxide, potassium hydroxide, sodium carbonate or sodium bicarbonate solution) at 50°C – 80°C for 1 – 2 hours and then treated with a proteolytic enzyme. In addition, hydrolyzates of casein or keratin may be employed.

The reaction between the amino acid, protein or peptide and the F.S.M.A may be conducted in an aqueous or non-aqueous solvent in the presence of a base. The acylation reaction will occur between $-5°$ and 40°C, and temperatures between 5° and 20°C are preferred. Best results are obtained when the reaction is carried out at a pH not exceeding 13.0, and preferably between about 11.0 and 13.0. Suitable bases include the inorganic bases, such as sodium, potassium or magnesium hydroxide, sodium carbonate and bicarbonate or the organic amines, such as triethylamine and pyridine.

After completion of the reaction, the reaction solution containing the desired product and sulfate salts may be directly employed as a liquid detergent by neutralization with sulfuric acid. Also, the reaction solution may be prepared in the form of a powdered detergent, for example by a process wherein it is concentrated to remove organic solvent therein and the residue is neutralized with an sulfuric acid and mixed with adequate additive, such as a perfume, and is subjected to spray-drying.

The desired product may be isolated from the reaction solution, if desired. For example, in the case where the desired product is N-acylamino acid, the reaction mixture is acidified to a pH of 3 to 1 with dilute sulfuric acid, whereby the N-acylamino acid is precipitated in the form of crystals which may be recovered by filtration or decantation. If the N-acylamino acid remains dissolved in the acidified reaction mixture, it may be crystallized by evaporation of the organic solvent. For isolation of acylated peptide or protein, the reaction mixture is acidified to pH 2 with dilute sulfuric acid and extracted with n-butyl alcohol, and then the desired product may be separated from the extract by evaporation of the organic solvent.

The following examples are further illustrative of this invention.

EXAMPLE 1

Lauric acid 20 g was dissolved in 80 ml 1.2-dichloroethane and then 10 g triethylamine was added. The resulting solution was held at $-2° – 5°C$ and 8 g sulfuric anhydride was added dropwise with stirring. The reaction mixture was stirred at that temperature for 50 minutes and a solution of lauric acid-sulfuric acid mixed acid anhydride was prepared and employed in the following acylation.

Sodium hydroxide 8 g was added to a suspension of 14.7 g L-glutamic acid in 72 ml water and 48 ml acetone. The resulting solution of disodium L-glutamate was cooled to 0°C and 10 ml of 10 N aqueous sodium hydroxide solution and the mixed acid anhydride prepared in the above was added drop by drop under stirring while the pH was controlled to 12 – 13. This reaction solution was stirred for 1 hour at 0°C. Thereafter, the reaction mixture was concentrated under reduced pressure to distill off the solvent. The residue was adjusted to a pH 1 with 6 N sulfuric acid.

The crude crystals of N-lauroyl-L-glutamic acid precipitated, and were filtered and dried (25.7 g). They were washed with petroleum benzine and 23.2 g of the purified acid were recovered by filtration (70.3% yield) M.P. 102° – 105°C. After recrystallization from ethanol-petroleum benzine, the elemental analysis was as follows:

|  | C % | H % | N % |
|---|---|---|---|
| Found: | 61.88 | 9.52 | 4.20 |

|  | C % | H % | N % |
|---|---|---|---|
| Calculated for $C_{17}H_{31}O_5N$: | 61.98 | 9.49 | 4.25 |

EXAMPLE 2

Lauric acid 20 g was dissolved in 120 ml 1.2-dichloroethane and then 10 g triethylamine was added. The mixture was held at 10° – 30°C while stirring and 8.8 g sulfuric anhydride was added dropwise. This solution was stirred at that temperature for 10 minutes to prepare lauric acid-sulfuric acid mixed acid anhydride.

Triethylamine 25 g was added to a suspension of 17.5 g DL-glutamic acid diethylester in 100 ml 1.2-dichloroethane. The mixture was held at −4° – 5°C while stirring, and the above solution of lauric acid-sulfuric acid mixed acid anhydride was added dropwise. The solution was stirred for 30 minutes.

The reaction mixture was twice washed with 200 ml water in a manner to separate 1.2-dichloroethane layer. The solvent was dried over Glauber's salt, and then concentrated to obtain 32.0 g crystals of N-lauroyl-DL-glutamic acid diethylester. 71.2% yield, M.P. 52° – 54°C. When recrystallization from mixed solvents of ethanol-water (3 : 7), they had the following elemental analysis:

|  | C % | H % | N % |
|---|---|---|---|
| Found: | 63.79 | 9.90 | 3.99 |
| Calculated for $C_{19}H_{35}O_5N$: | 63.83 | 9.87 | 3.92 |

EXAMPLE 3

Sulfuric anhydride (8 g) was added dropwise to a solution of 25.6 g palmitic acid dissolved in 200 ml carbon tetrachloride at −5° – 0°C while stirring. Thereafter, the reaction solution was stirred for 40 minutes. This solution was used in the following acylation.

Sodium hydroxide 8 g was added to a suspension of 13.3 g L-aspartic acid in 72 ml water and 48 ml acetone to form a solution of disodium L-aspartate. This solution was held at 0°C, and the solution of palmitic acid-sulfuric acid mixed acid anhydride and a solution of 12 g sodium hydroxide in 30 ml water was added dropwise simultaneously with stirring. This solution was stirred for 1 hour at 0°C.

The reaction mixture was concentrated under reduced pressure to remove the organic solvents and the residue was acidified to pH 1 with 6 N sulfuric acid. Crude crystals of N-palmitoyl-L-aspartic acid precipitated, and were filtered and dried (20.5 g). They were washed with petroleum benzene and 15.3 g of the pure acid were recovered by filtration (41.3% yield), M.P. 124° – 125°C.

EXAMPLE 4

Sulfuric anhydride dioxane complex prepared from 9.6 g sulfuric anhydride and 10.6 g dioxane was added dropwise to a solution of 20 g lauric acid in 200 ml carbon tetrachloride at −5° – 0°C while stirring.

This solution was stirred at that temperature for 20 minutes, to prepare lauric acid-sulfuric acid mixed acid anhydride for use in the following acylation.

Potassium hydroxide 11.3 g was added to a suspension of 13.3 g DL-aspartic acid in a mixed solvent of 60 ml ethyl alcohol and 60 ml water to form a solution of dipotassium DL-aspartate. To the ice-cooled resultant solution a solution of lauric acid-sulfuric acid mixed acid anhydride and 10 ml of 10 N potassium hydroxide was added dropwise simultaneously with stirring. While the pH was controlled to 12 stirring at room temperature was then continued for 1 hour. The reaction mixture was treated in the similar manner as in Example 3 to obtain 14.3 g crude crystals of N-lauroyl-DL-aspartic acid.

EXAMPLE 5

Pyridine (8 g) was added to a solution of 20 g lauric acid in 100 ml 1.2-dichloroethane. While the mixture was held at 5° – 10°C while stirring, 8 g sulfuric anhydride was added dropwise. The solution was continued stirring for 25 minutes to prepare lauric acid-sulfuric acid-mixed acid anhydride for use in the following acylation.

DL-alanine (8.9 g) was dissolved in a mixture of 10 ml 10 N sodium hydroxide and 100 ml water.

The resultant solution was ice-cooled while stirring, and then the solution of lauric acid-sulfuric acid mixed acid anhydride prepared in the above and 10 ml 10 N sodium hydroxide was added dropwise simultaneously while the pH was controlled to 13. After stirring at room temperature for 1 hour, the reaction mixture was divided into two layers of water and 1.2-dichloroethane. The water layer separated was acidified to pH 1 with 6 N sulfuric acid. The precipitated crude crystals of N-lauroyl-DL-alanine were filtered and dried, and then washed with petroleum benzine, yield 17.1 g (63%). M.P. 106° – 107°C.

EXAMPLE 6

Trimethylamine (6 g) was added to a solution of 19.3 g coconut oil fatty acid in 100 ml 1.2-dichloroethane. While the mixture was held at 10° – 20°C while stirring, 8 g sulfuric anhydride was added dropwise. The solution was continued stirring for 10 minutes and coconut oil fatty acid-sulfuric acid mixed acid anhydride was prepared and employed in the following acylation.

A suspension of 14.7 g L-glutamic acid in 120 ml in a water-acetone mixed solvent (1 : 1 by volume) was mixed with 20 ml 10 N sodium hydroxide. The resultant solution was ice-cooled and, the coconut oil fatty acid-sulfuric acid mixed acid anhydride and 10 N sodium hydroxide were added dropwise simultaneously while the pH was controlled to 13 while stirring. After stirring at room temperature for 1 hour, the reaction mixture was concentrated under reduced pressure to remove the organic solvents. The residue was adjusted to pH 6 with 6 N sulfuric acid and then mixed with a small amount of perfume to prepare a liquid detergent.

EXAMPLE 7

Sulfuric anhydride (8 g) was added to a solution of 26 g hydrogenated tallow fatty acid in 150 ml dioxane at −3° – 3°C under stirring. Thereafter stirring was continued for an additional 10 minutes to prepare hydrogenated tallow fatty acid-sulfuric acid mixed acid anhydride for use in the following acylation.

Glycine 7.5 g and 33.6 sodium bicarbonate were dissolved in 150 ml water and then the mixed acid anhydride prepared in the above was added dropwise thereto under ice-cooling while stirring was operated. After stirring for further 1 hour, the reaction mixture was acidified to pH 1 with 6 N sulfuric acid and concentrated under reduced pressure to remove dioxane. The precipitated hydrogenated tallowyl glycine were filtered off and dried. Yield 18.6 g (51.8%)

EXAMPLE 8

Magnesium stearate 31 g was suspended in 300 ml toluene and reacted while 9.6 g sulfuric anhydride at 0° – 5°C with stirring. The solution was continued stirring for 20 minutes. There was obtained a solution of stearic acid-sulfuric acid mixed acid anhydride which was employed in the following acylation.

L-Phenylalanine 16.5 g and 31.8 g sodium carbonate were dissolved in 100 ml water. The solution of stearic acid-sulfuric acid mixed acid anhydride was ice-cooled with stirring. The reaction mixture was treated in the similar manner as in Example 7 to 12.2 g N-stearoyl-L-phenylalanine. M.P. 96° – 97°C.

EXAMPLE 9

Sulfuric anhydride dimethylformamide complex prepared from 8.8 g sulfuric anhydride and 10 g dimethylformamide was added dropwise to a solution of 22.8 g myristic acid in 200 ml dimethylformamide at 0° – 5°C while stirring.

The resulting solution of myristic acid-sulfuric acid mixed acid anhydride was reacted with 11.7 g L-valine in the similar manner as in Example 8 to obtain 19.6 g (59.8%) N-myristoyl-L-valine. M.P. 88° – 89°C.

EXAMPLE 10

Sulfuric anhydride 8 g was added dropwise to a solution of 20 g lauric acid in 100 ml 1.2-dichloroethane at –5° – 0°C with stirring. Immediately after the addition of sulfuric anhydride, 10 g triethylamine was added. The mixture was stirred at room temperature for 30 minutes and then employed in the following acylation.

DL-Glutamic acid 14.7 g were suspended in a mixture of 150 ml water and 150 ml acetone and reacted with lauric acid-sulfuric acid mixed acid anhydride prepared in the above in the similar manner as in Example 1. There was obtained 20 g N-lauroyl-DL-glutamic acid.

EXAMPLE 11

Sulfuric anhydride 16 g and 20 g triethylamine were added dropwise simultaneously to a solution of 51.2 g palmitic acid in 200 ml 1.2-dichloroethane at –5° – 0°C while stirring. Stirring of the solution was continued at room temperature for 30 minutes and the resulting palmitic acid-sulfuric acid mixed acid anhydride was employed in the following reaction.

L-Lysine hydrochloride 18.3 g was dissolved in 100 ml water and neutralized with 20 ml 10 N sodium hydroxide. The palmitic acid-sulfuric acid mixed acid anhydride was added dropwise at 0° – 5°C with stirring. The reaction mixture was treated in a similar manner as in Example 10 to obtain 39.4 g (63.2% yield) N.N-dipalmityl-L-lysine. M.P. 124° – 125°C.

EXAMPLE 12

Sulfuric acid 9.8 g and 100 ml toluene were added to a mixture of 14.7 g L-glutamic acid and 58 g cetyl alcohol and the esterification reaction was conducted according to the azeotropic dehydration method. After removal of solvents from the esterified reaction mixture, the residue was dissolved in a mixture of 100 ml chloroform and 20 g triethylamine. The resultant solution of L-glutamic acid dicetylester was reacted in the similar manner as in Example 2 with lauric acid-sulfuric acid mixed acid anhydride which had been prepared by adding 8 g sulfuric anhydride to a solution of 20 g lauric acid in a mixture of 80 ml chloroform and 10 g triethylamine at –2° –5°C with stirring. There was obtained 41.3 g (83.3% yield) pale yellowish and wax-like N-lauroyl-L-glutamic acid dicetylester.

EXAMPLE 13

Sulfuric anhydride 8 g was added dropwise to a solution of 10 g triethylamine in 120 ml 1.2-dichloroethane while the solution was held at 0° – 10°C while stirring. Then 25.6 g palmic acid was added thereto. The mixture was stirred for 15 minutes to prepare palmitic acid-sulfuric acid mixed acid anhydride, which was employed in the following acylation.

Aqueous peptide solution 2 l was prepared by subjecting 45 g casein to partial hydrolysis with proteolytic enzyme by the manner described in Referential Example (1) and mixed with 600 ml acetone and then adjusted to pH 12 with 28% sodium hydroxide. To the resultant solution under ice-cooling with stirring, the solution of palmitic acid-sulfuric acid mixed acid anhydride and 28% sodium hydroxide were added simultaneously and dropwise while the pH was controlled to 12 – 13. After stirring for 1 hour, the reaction mixture was acidified to pH 2 with dilute hydrochloric acid and extracted twice with 3 l n-butanol. And then, organic solvent layers were combined and concentrated under reduced pressure to 100 ml.

Ether 1 l was added thereto and crystals of palmityl peptide precipitated, and were filtered off and dried (21 g).

This product showed negative ninhydrin reaction and an aqueous solution of its sodium salt had the following surface active properties.

Surface tension of 44.5 dyne/cm (0.25%, 40°C)

Foaming power of 95 mm (value after 10 minutes in foam height measured according to Ross Mills method)

EXAMPLE 14

Sulfuric anhydride 2 g was added dropwise to a solution of 5.0 g lauric acid in 100 ml carbon tetrachloride while the solution was stirred at –5° – 0°C. Stirring was continued for 30 minutes and there was prepared a solution of lauric acid-sulfuric acid mixed acid anhydride.

To 5 g peptide prepared by partial hydrolysis of soybean protein with hydrochloric acid, 100 ml water, 75 ml acetone and 28% sodium hydroxide were added to bring the pH to 12. Then, the lauric acid-sulfuric acid mixed acid anhydride solution and 28% sodium hydroxide were added simultaneously and dropwise under ice-cooled conditions with stirring while the pH was maintained at 12 – 13. After stirring for an additional 30 minutes, the reaction mixture was acidified to a pH of 2 with dilute sulfuric acid and treated in a similar manner as in Example 13, to obtain 3 g lauroyl peptide.

EXAMPLE 15

Sulfuric anhydride 4 g was added dropwise to a solution of 12.8 g palmitic acid and 9.3 g tributylamine in 60 ml 1.2-dichloroethane at –5° – 5°C while stirring. Stirring was continued at the room temperature for 30 minutes. There was prepared a solution of palmitic acid-sulfuric acid mixed acid anhydride which was employed in the following acylation.

L-Valylvaline 10.8 g were mixed with a mixture of 500 ml water, 500 ml acetone and 28% sodium hydroxide to form a solution of pH 12. Thereafter, the palmitic acid-sulfuric acid mixed acid anhydride solution and 8.5 ml 28% sodium hydroxide were added simultaneously and dropwise under ice-cooled conditions with stirring while the pH was adjusted to 12 – 13.

After stirring for further 1 hour, the reaction mixture was acidified to pH 2 with dilute sulfuric acid and extracted with ethyl acetate. The ethyl acetate extract was washed with water and dried over Glauber's salt, and then concentrated to evaporate the organic solvents. 12.5 g N-palmityl-L-valylvaline were obtained. M.P. 120° – 123°C.

EXAMPLE 16

Sulfuric acid 4 g was added dropwise to a solution of 9.6 coconut oil fatty acid and 5 g triethylamine in 100 ml 1,2-dichloroethane with stirring while the solution was held at 5° – 10°C. Stirring was continued for 15 minutes and there was prepared a solution of coconut oil fatty acid-sulfuric acid mixed acid anhydride which was employed in the following acylation.

400 ml aqueous solution containing 10 g peptide which had been prepared by decomposing casein with protease were adjusted to pH 10 with 28% sodium hydroxide. Thereafter, the coconut oil fatty acid-sulfuric acid mixed acid anhydride solution and 8.5 ml 28% aqueous sodium hydroxide solution were added simultaneously and dropwise with stirring at 5° – 15°C while the pH was controlled to 10 – 12. After stirring at room temperature for 2 hours, the reaction mixture was adjusted to pH 7 with dilute sulfuric acid and concentrated under reduced pressure to remove 1,2-dichloroethane. There was obtained an aqueous solution of coconut oil fatty acid acyl peptide whose surface active properties were as follows: Surface tension of 40.2 dyne/cm (40°C)

Foaming power of 152 mm (foam height after 5 minutes measured according to Ross Mills method)

EXAMPLE 17

Sulfuric anhydride-dioxane complex which had been prepared from 4.8 g sulfuric acid was added drop by drop to a solution of 11.4 g myristic acid in 200 ml carbon tetrachloride while stirring at 0° – 5°C. Stirring was continued for 40 minutes and there was prepared a solution of myristic acid-sulfuric acid mixed acid anhydride which was employed in the following acylation.

Aqueous solution 700 ml containing 25 g peptide derived from gelatin by partial hydrolysis with hydrochloric acid was adjusted to pH 12 with 6 N potassium hydroxide. And then the mixed acid anhydride solution prepared in the above and 10 ml 6 N aqueous potassium hydroxide solution were added simultaneously and dropwise with stirring at 10° – 20°C while the ph was controlled to 11 – 12. After stirring at room temperature for an additional hour, the reaction mixture was acidified to pH 1 with hydrochloric acid and extracted with 800 ml n-butylalcohol in the similar manner as in Example 13. 8 g myristyl peptide were obtained.

EXAMPLE 18

The procedure of Example 13 was repeated except that hydrogenated tallow fatty acid was employed instead of palmitic acid. There was obtained 8.6 g hydrogenated tallow fatty acid acyl peptide.

EXAMPLE 19

The procedure of Example 16 was repeated except that soybean protein, "Ajipron 90" (trade name, a product of Ajinomoto Co., Inc.) was employed instead of peptide prepared by hydrolysys of casein to obtain 18.3 g coconut oil fatty acid acyl soybean protein. Its aqueous solution had good surface active properties for use s detergent.

EXAMPLE 20

Lauric acid 20 g was dissolved in 80 ml of 1,2-dichloroethane. To the solution, 8 g of sulfuric anhydride were added dropwise at −2° – −5°C with stirring, then neutralized with 10 g of triethylamine. Stirring of the solution was continuted for an additional 20 minutes.

DL-Glutamic acid 14.7 g was suspended in 75 ml water and 45 ml acetone and then added 8 g of sodium hydroxide. To the solution of the sodium glutamate was added lauric acid-sulfuric acid mixed anhydride with 10 N sodium hydroxide at pH 12 – 13 on the ice bath with stirring. The reaction mixture was stirred for an additional 1 hour, then treated by the same manner as in Example 1. N-Lauroyl-DL-glutamic acid was obtained 19.7 g (59.7 %) M.P. 116° – 119°C.

EXAMPLE 21

Palmitic acid 12.8 g was dissolved in 60 ml of 1,2-dichloroethane and 5 g of triethylamine. To the solution, 4 g of sulfuric anhydride was added dropwise at −4° – 2°C while stirring. The solution was continuted stirring for additional 20 minutes, then filtered. The filtrate was concentrated under reduced pressure. Petroleum benzine 300 ml was added to the residue, and the palmitic acid sulfuric acid mixed anhydride was crystallized. 15 g (68.6%) mp 56° – 58°C.

L-Glutamic acid 2.9 g was dissolved in 30 ml water and 30 ml methanol and 1.6 g of sodium hydroxide. To this solution was added 8.8 g of the crystal of palmitic acid sulfuric acid mixed anhydride and 10 N sodium hydroxide to keep pH 12 to 13, with stirring at 21° – 22°C. The reaction mixture was stirred for an additional 1 hour, and then treated by the same manner as in Example 1. N-Lauroyl-L-glutamic acid was obtained. Yield 6.4 g (96.9%). M.P. 101° – 104.5°C.

EXAMPLE 22

To a solution of 1,2-dichloroethane 100 ml and lauric acid 10 g was added dropwise sulfuric anhydride 4 g at −2° – 6°C with stirring. Then the reaction mixture was stirred for an additional 25 minutes. To 175 ml peptide solution which was obtained from microorganism by the procedure of Referential example(3) and which was adjusted to pH 12, was added lauric acid sulfuric acid mixed acid anhydride at 10° – 24°C with stirring, to keep pH 11 – 12 with sodium hydroxide. After stirring for 45 minutes, was treated by the same manner as in Example 17. Lauroyl peptide was obtained. Yield 16 g.

REFERENCE EXAMPLE: partial hydrolysis of protein

1. Casein 45 g was mixed with 450 ml water and adjusted to pH 10 with 6 N sodium hydroxide and mixed with 0.45 g proteolytic enzyme, "asterase" (trade name, a product of Ajinomoto Co., Inc.). The mixture was heated at 55°C and at a pH of 9.0 – 10.0 for 4 hours. The hydrolyzate obtained was diluted with water to 2 l and thereafter a small amount of insoluble material was filtered off and the filtrate was employed in the acylation.

2. Soybean protein 100 g ("Ajipron 90" trade name, a product of Ajinomoto Co., Inc.) were dissolved 300 ml water and acidified to pH 1.5. The acidified solution was heated at 100°C for 20 hours and concentrated under reduced pressure to obtain protein hydrolyzate.

3. Microorganism 150 g (containing water 57.1 %) separated from glutamic acid fermentation, was added to a mixture of 300 ml of water and 22.6 g of sodium hydroxide, then heated at 90°C, for 7 hours. The solution was filtered and then analyzed average peptide length (A.P.L.) by the ratio of $NH_2$—N and total N. The A.P.L. was 3.65.

What we claim is:

1. A process for preparing N-higher aliphatic acyl derivatives of amino acids, peptides or proteins which comprises the following steps: (1) reacting a mole of a tertiary amine salt of a fatty acid having 6 to 22 carbon atoms with 1 to 2 moles of sulfuric anhydride or complex thereof at a temperature ranging from −20°C to 40°C in a non-aqueous solvent to form a mixed acid anhydride of a fatty acid having 6 to 22 carbon atoms and sulfuric acid and subsequently (2) reacting the mixed acid anhydride prepared with an amino acid, peptide or protein in a liquid medium in the presence of base at temperatures between −5°C and 40°C until the corresponding N-acylated product is formed.

2. The process as set forth in claim 1, wherein said fatty acid is caprylic acid, capric acid, lauric acid, myristic acid, palmitric acid, stearic acid, oleic acid, linoleic acid, coconut oil fatty acid, tallow fatty acid or hydrogenated tallow fatty acid.

3. The process as set forth in claim 1, wherein said salt of said fatty acid is the trimethylamine, triethylamine or pyridine salt thereof.

4. The process as set forth in claim 1, wherein said sulfuric anhydride complex is dioxane-sulfur trioxide complex, dimethylformamide-sulfur trioxide complex, dimethylaniline-sulfur trioxide complex or pyridine-sulfur trioxide complex.

5. The process as set forth in claim 1, wherein said amino acid is taurine, glycine, $\alpha$-alanine, $\beta$-alanine, sarcosine, valine, leucine, isoleucine, methionine, cystine, cysteine, phenylalanine, tyrosine, tryptophan, threonine, serine, proline, $\omega$-aminocaproic acid glutamic acid, aspartic acid, oxyglutamic acid, methylglutamic acid, cysteic acid, homocysteic acid, lysine, ornithine, histidine, arginine, or mixtures thereof.

6. The process as set forth in claim 1, wherein said peptide contains an average of 2 to 12 amino acid units.

7. The process as set forth in claim 1, wherein said protein is casein, gelatin, yeast, soybean protein or the extracted protein of a microorganism.

8. The process as set forth in claim 1, wherein said base is sodium hydroxide, potassium hydroxide, sodium carbonate, sodium bicarbonate, trimethylamine, triethylamine or pyridine.

9. The process as set forth in claim 1, wherein said medium contains an amount of base sufficient to make the pH thereof 11.0 to 13.0.

10. The process as set forth in claim 1, wherein the N-acylated product is recovered from said medium.

* * * * *